US011826562B2

(12) United States Patent
Rock et al.

(10) Patent No.: US 11,826,562 B2
(45) Date of Patent: Nov. 28, 2023

(54) IMPLANTABLE MEDICAL LEAD

(71) Applicant: Medtronic, Inc., Minneapolis, MN (US)

(72) Inventors: Kaileigh E. Rock, Saint Paul, MN (US); Mark T. Marshall, Cape Coral, FL (US); Lonnie D. Ronning, Coon Rapids, MN (US); Dina L. Williams, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 101 days.

(21) Appl. No.: 17/322,158

(22) Filed: May 17, 2021

(65) Prior Publication Data

US 2021/0379367 A1 Dec. 9, 2021

Related U.S. Application Data

(60) Provisional application No. 63/036,569, filed on Jun. 9, 2020.

(51) Int. Cl.
*A61N 1/05* (2006.01)
*A61N 1/375* (2006.01)

(52) U.S. Cl.
CPC ....... *A61N 1/0573* (2013.01); *A61N 1/37518* (2017.08)

(58) Field of Classification Search
CPC .............. A61N 1/0573; A61N 1/37518; A61N 1/0558; A61N 1/059
See application file for complete search history.

(56) References Cited

U.S. PATENT DOCUMENTS

| 8,112,160 B2 | 2/2012 | Foster |
| 2003/0144722 A1 | 7/2003 | Soltis et al. |
| 2019/0022379 A1* | 1/2019 | Foster .................... A61N 1/375 |
| 2020/0114146 A1* | 4/2020 | Foster ................ A61N 1/37205 |

FOREIGN PATENT DOCUMENTS

AU 2018204610 A1 2/2019

OTHER PUBLICATIONS

International Search Report and Written Opinion of International Application No. PCT/US2021/034157, dated Sep. 9, 2021, 14 pp.

* cited by examiner

*Primary Examiner* — Eugene T Wu
(74) *Attorney, Agent, or Firm* — Shumaker & Sieffert, P.A.

(57) ABSTRACT

An implantable medical lead comprising one or more tines configured to extend and/or retract from a lead body. The implantable medical lead includes a torque member within the implantable medical lead and configured to rotate a drive shaft within the implantable medical lead. The drive shaft is threadably engaged with an interior surface of the implantable medical lead and configured to convert the rotation into a lateral translation of the drive shaft. The one or more tines are configured such that the lateral translation of the torque member laterally translates the one or more tines. The one or more tines are each electrically connected to a conductor extending through a lumen of the implantable medical lead and electrically isolated from each other.

20 Claims, 5 Drawing Sheets

IMPLANTABLE MEDICAL LEAD

This application claims the benefit of U.S. Provisional Patent Application Ser. No. 63/036,569 (filed Jun. 9, 2020), which is entitled, "IMPLANTABLE MEDICAL LEAD" and is incorporated by reference herein in its entirety.

TECHNICAL FIELD

This disclosure is related to medical devices such as implantable medical leads.

BACKGROUND

Various types of implantable medical leads have been implanted for treating or monitoring one or more conditions of a patient. Such implantable medical leads may be adapted to allow medical devices to monitor or treat conditions or functions relating to heart, muscle, nerve, brain, stomach, endocrine organs or other organs and their related functions. Implantable medical leads include electrodes and/or other elements for physiological sensing and/or therapy delivery. Implantable medical leads allow the sensing/therapy elements to be positioned at one or more target locations for those functions, while the medical devices electrically coupled to those elements via the leads are at different locations.

Implantable medical leads, e.g., distal portions of elongated implantable medical leads, may be implanted at target locations selected to detect a physiological condition of the patient and/or deliver one or more therapies. For example, implantable medical leads may be delivered to locations within an atria or ventricle to sense intrinsic cardiac signals and deliver pacing or antitachyarrhythmia shock therapy from a medical device coupled to the lead. In other examples, implantable medical leads may be tunneled to locations adjacent a spinal cord or other nerves for delivering pain therapy from a medical device coupled to the lead. Implantable medical leads may include anchoring components to secure a distal end of the lead at the target location.

SUMMARY

An implantable medical lead comprises a lead body comprising an interior surface with the interior surface defining a lumen. The lead body defines a longitudinal axis extending through the lumen. The lead includes a drive shaft configured to threadably engage the interior surface, and a torque member configured to rotate the drive shaft around the longitudinal axis. The drive shaft is configured to translate in a direction substantially parallel to the longitudinal axis when the torque member rotates the drive shaft. The lumen is sized to allow passage of the torque member and at least a portion of the drive shaft therethrough.

The lead further comprises one or more tines mechanically coupled to the drive shaft. The one or more tines are configured to at least partially extend out of the lead body when the torque member rotates the drive shaft in a first direction and at least partially retract into the lumen when the torque member rotates the drive shaft in a second direction. The tines may be coupled to one or more electrical conductors that extend through the lead body, and thereby act as electrodes for sensing and/or therapy. In some examples, each tine is coupled to a respective one or more conductors and is separately activatable.

In an example, the drive shaft is configured to rotate relative to the interior surface of the lumen and relative to the one or more tines when the torque member rotates the drive shaft. In an example, the drive shaft is configured to rotate relative to the interior surface of the lumen when the torque member rotates the drive shaft, and the one or more tines are rotationally coupled with the drive shaft such that the one or more tines rotate relative to the interior surface of the lumen.

A technique for inserting one or more tines of an implantable medical lead in patient tissue at a target location includes rotating a torque member within a lumen of lead body around a longitudinal axis, wherein an interior surface of the lead body defines the lumen. The technique includes rotating a drive shaft rotationally coupled to the torque member using the rotation of the torque member. The technique includes threadably engaging the drive shaft and the interior surface, and converting the rotation of the drive shaft into a lateral translation of the drive shaft using the threaded engagement. The technique includes extending one or more tines from the lead body by translating the one or more tines using the lateral translation of the drive shaft. The technique may include retracting the one or more tines into the lead body using the lateral translation of the drive shaft.

The details of one or more examples are set forth in the accompanying drawings and the description below. Other features, objects, and advantages will be apparent from the description and drawings, and from the claims.

DETAILED DESCRIPTION

Figure 1:
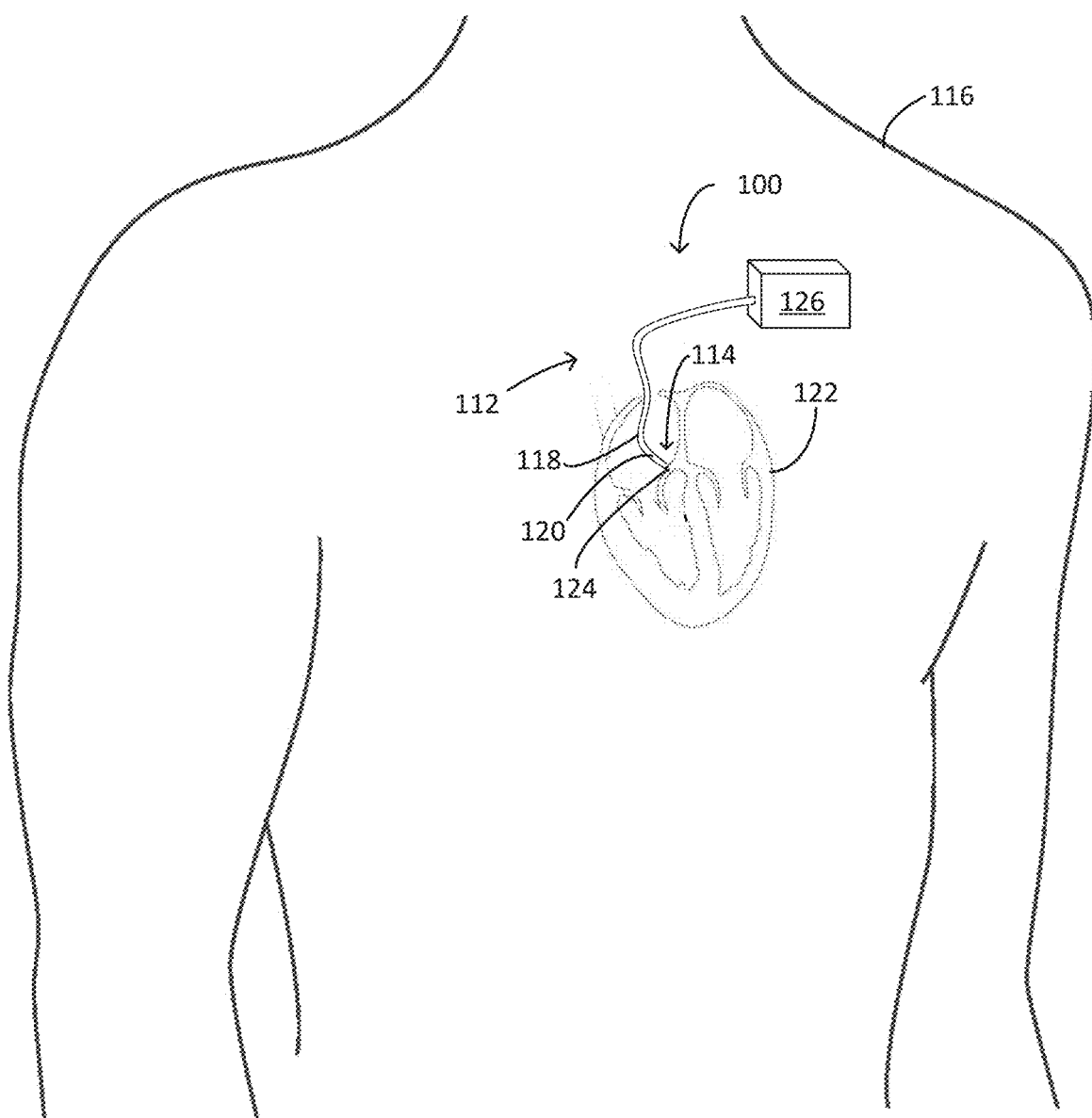
FIG. 1 is a conceptual diagram illustrating an example implantable medical lead implanted at an example target site.

This disclosure describes an implantable medical lead configured to deliver tines that penetrate the tissue at a target site within a patient. The implantable medical lead includes a lead body having one or more tines configured to extend and/or retract from the lead body. One or more tines may be configured to penetrate the tissue at the target site to substantially anchor the lead. For example, one or more tines may be configured to penetrate into cardiac tissue at or near a target site, such as tissues of the left bundle branch (LBB), His bundle (HB), right bundle branch (RBB), and other ventricular and/or cardiac tissues of the patient's heart.

In general, a tine may refer to any structure that is capable of securing a lead or leadless implantable medical device to a location within the heart. In some examples, a tine may be composed of a shape-memory allow that allows deformation along the length of the tine. A tine may be substantially flat along the length of the tine. In other examples, a tine may substantially define a helix and/or helical member. In some examples, the tines may include a combination of different shapes, e.g., one or more substantially flat tines and one or more helical tines.

In some examples, the tines are configured to function as an electrode to provide electrical stimulation therapies to the tissue. The tines may be configured such that their electrically active portions, e.g., distal ends, are spaced apart from one another in the cardiac tissue. In some examples, one or more tines in a plurality of tines are electrically isolated from each other and selectable such that each tine may individually deliver electrical stimulation. The tines may be electrically connected to a conductor (e.g., a multi-conductor) for delivery of the stimulation from therapy delivery circuitry of a medical device to an individual tine. In some examples, the conductor may be connected to only some of the one or more of the tines. In some examples, the implantable medical lead may not include a conductor electrically connected to the one or more tines.

The tines are configured to be extendable and/or retractable from the lead body to facilitate penetration of tissues in the vicinity of the target site. The extension and/or retraction of the tines may be controlled by a clinician. The ability to extend or retract the tines may allow the clinician to produce an evoked response at a particular location, e.g., tissues of the left bundle branch (LBB), His bundle (HB), right bundle branch (RBB), and other ventricular and/or cardiac tissues of the patient's heart.

The medical lead includes a torque member extending through a lumen of the lead body and rotationally coupled to a drive shaft within the lumen. The drive shaft includes a set of external threads threadably engaged with a set of internal threads on a lead interior surface surrounding the lumen. Rotation of the torque member causes rotation of the drive shaft, and the threadable engagement of the drive shaft and the lead interior surface causes a lateral translation of the drive shaft with respect to the lead interior surface. The tines are mechanically coupled to the drive shaft, such that the lateral translation of the drive shaft causes a lateral translation of the tines. In this manner, rotation of the torque member may cause an extension and/or retraction of the tines from or into the medical lead.

In some examples, the tines are configured such that the drive shaft rotates relative to the tines and the tines remain rotationally stationary as the drive shaft acts to extend and/or retract the tines. In some examples, the tines are configured to be rotationally coupled with the drive shaft, such that the tines rotate with the drive shaft as the drive shaft acts to extend and/or retract the tines. The tines may be resiliently biased to expand radially outward when the tines are extended. In some examples, the tines include one or more helical members configured to expand radially as the tines are extended.

FIG. 1 is a conceptual diagram illustrating a portion of an example medical device system 100 including an implantable medical lead 112 positioned at a target site 114 within a patient 116. Implantable medical lead 112 includes an elongated lead body 118 with a distal portion 120. Distal portion 120 may be, for example, a sleeve head of implantable medical lead 112. In some examples, as illustrated in FIG. 1, the target site 114 may include a portion of a heart 122, such as an atrioventricular septal wall of a right atrium (RA) of heart 122, as illustrated in FIG. 1, or interventricular septal wall of a right ventricle (RV) of heart 122, or other locations within a body of patient 116. A clinician may maneuver distal portion 120 through the vasculature of patient 116 in order to position distal portion 120 at or near target site 114. For example, the clinician may guide distal portion 120 through the superior vena cava (SVC) and into the RA, in order to access target site 114 on the atrioventricular septal wall, e.g., in the triangle of Koch region. In some examples, other pathways or techniques may be used to guide distal portion 120 into other target implant sites within the body of patient 116. Medical device system 100 may include a delivery catheter and/or outer member (not shown), and implantable medical lead 112 may be guided and/or maneuvered within a lumen of the delivery catheter in order to approach target site 114.

For example, in one or more embodiments described herein, target site 114 may be the triangle of Koch region in the atrioventricular septal wall of the patient's heart or the ventricular septal wall in the basal (e.g., high basal or high septal) region or apical (e.g., low septal or near the apex) region. Implantation in the triangle of Koch region of the atrioventricular septal wall may facilitate pacing of the His bundle or ventricular myocardium. Implantation in the basal region of the ventricular septal wall may facilitate pacing of the His bundle branches. Implantation in the apical region may facilitate pacing of Purkinje fibers.

Implantable medical lead 112 includes tine 124 configured to penetrate cardiac tissue at or near target site 114. For example, tine 124 of implantable medical lead 112 may be configured to penetrate to a position at or near the left bundle branch (LBB), His bundle (HB), right bundle branch (RBB), other specialized conductive tissue, or other ventricular tissue of heart 122. In some examples, tine 124 is configured to function as an electrode in order to, for example, provide pacing to heart 122. Tine 124 may be electrically connected to a conductor (not shown) extending through implantable medical lead 112 from tine 124. In examples, the conductor is electrically connected to therapy delivery circuitry of an implantable medical device (IMD) 126, with the therapy delivery circuitry configured to provide electrical signals through the conductor to tine 124. Tine 124 may conduct the electrical signals to the target tissue of heart 122, causing the cardiac muscle, e.g., of the ventricles, to depolarize and, in turn, contract at a regular interval. In examples in which tine 124 penetrates to a position at or near the HB, RBB, LBB, or other specialized conductive tissue of heart 122, the cardiac pacing delivered via tine 124 may be conduction system pacing (CSP) of heart 122, which may provide more physiologic activation and contraction of heart 122. Tine 124 may also be connected to sensing circuitry of IMD 126 via the conductor, and the sensing circuitry may sense electrical activity of heart 122 via tine 124.

In some examples, tine 124 is configured to be extendable and/or retractable with respect to lead body 118, in order to facilitate penetration of the cardiac tissue in the vicinity of target site 114. The lead body 118 may allow tine 124 to be placed deeper into the tissue and to provide multiple tines (electrodes) at different locations. The extension and/or retraction of tine 124 may be controlled by a clinician. As will be discussed, implantable medical lead 112 may be configured such that rotation of a torque member (not shown) within implantable medical lead 112 causes a lateral translation of tine 124, extending or retracting tine 124 from lead body 118 (e.g., from distal portion 120). Implantable medical lead 112 may be configured such that extension and/or retraction of tine 124 occurs over a substantially continuous range, so that a clinician may utilize the torque member to establish a particular depth of penetration of tine 124 into the cardiac tissue. In some examples, another medical device capable of being electrically connected to implantable medical lead 112 during implantation, such as a pacing system analyzer, may be configured to take electrical measurements during penetration of tine 124 into the cardiac tissue in order to, for example, determine a suitable location with the cardiac tissue for CSP of heart 122.

Tine 124 may be one of a plurality of tines, with tines in the plurality configured in a similar manner to tine 124. In some examples, one or more tines in the plurality of tines is electrically connected to a conductor, and each tine in the plurality is electrically isolated from every other tine in the plurality. One or more of the tines, such as tine 124, may be configured to substantially anchor implantable medical lead 112 to the penetrated cardiac tissue. In some examples, tine 124 includes a fixed end connected to implantable medical lead 112 and a free end configured to penetrate the cardiac tissue, and tine 124 is biased such that the extension of tine 124 causes the free end to deflect radially outward as tine 124 is extended. In some examples, tine 124 is a helical member which expands radially as tine 124 is extended.

Figure 2:
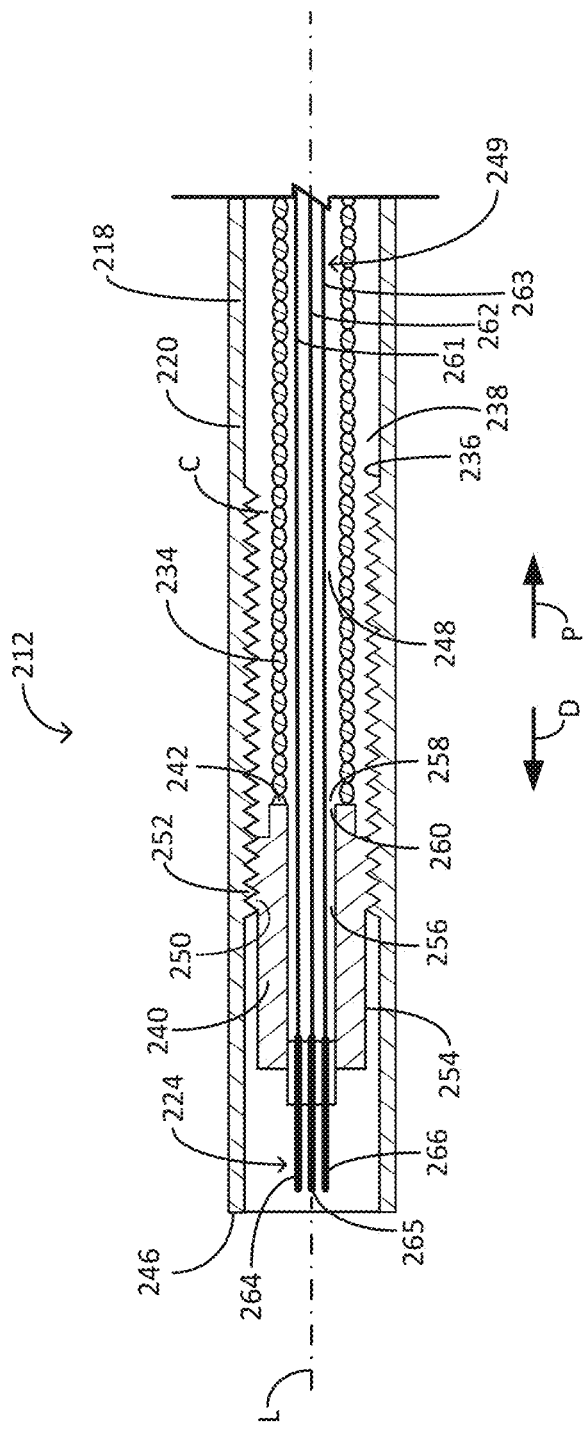
FIG. 2 is a plan view with selected cross-sections illustrating an example implantable medical lead.

FIG. 2 is a conceptual diagram illustrating a plan view of a portion of implantable medical lead 212. Implantable medical lead 212 is an example of implantable medical lead 112 (FIG. 1). Implantable medical lead 212 includes lead body 218, distal portion 220, one or more tines 224 ("tines 224"), and torque member 234, which may be configured similarly to and operate relative to other implantable medical lead 212 components in the same manner as the like-named components of implantable medical lead 112 Lead body 218 defines a longitudinal axis L. FIG. 2 illustrates longitudinal cross-sections of lead body 218, distal portion 220, and torque member 234, with a cutting plane taken parallel to the page.

Lead body 218 comprises an interior surface 236 ("lead interior surface 236") defining a lumen 238. Lead body 218 may be configured such that lumen 238 extends through at least distal portion 220 and may surround longitudinal axis L within distal portion 220. Lead interior surface 236 may be configured such that distal portion 220 of lead body 218 ("lead body distal portion 220) surrounds a segment of longitudinal axis L. Lead body 218 may be configured with any axial cross-section (e.g., a cross-section perpendicular to the longitudinal cross-section) sufficient to define lumen 238, and may define lumen 238 to have any suitable shape. For example, lead body 218 may define lumen 238 to include a circular, oval-shaped, polygonal, or other shape, and may include straight and curved segments. Lead body 218 may define lumen 238 to extend over substantially all or some portion of a length of lead body 218.

Implantable medical lead 212 includes a drive shaft 240 and torque member 234 within lumen 238. Drive shaft 240 is rotationally coupled to torque member 234, such that a rotation of torque member 234 around longitudinal axis L causes a rotation of drive shaft 240 around longitudinal axis L. In examples, torque member 234 is rotationally coupled to drive shaft 240 such that, when torque member 234 rotates about longitudinal axis L, drive shaft 240 rotates synchronously with torque member 234 about longitudinal axis L. As will be discussed, drive shaft 240 is configured to convert a rotation about longitudinal axis L into a lateral translation of drive shaft 240 in a direction substantially parallel to longitudinal axis L. Drive shaft 240 is further configured such that the lateral translation of drive shaft 240 laterally translates tines 224 in the direction substantially parallel to longitudinal axis L. Thus, implantable medical lead 212 is configured such that a rotation of torque member 234 causes a rotation of drive shaft 240, generating a lateral translation of drive shaft 240 and tines 224. Consequently, drive shaft 240 and torque member 234 may be configured such that rotation of torque member 234 generates extension and/or retraction of tines 224 from lead body 218. In an example, rotation of torque member 234 in a first direction around longitudinal axis L causes lateral translation of tines 224 in a distal direction D (e.g., a direction toward distal end 246 of lead body 218 ("lead body distal end 246"), and rotation of torque member 234 in a second direction opposite the first direction around longitudinal axis L causes lateral translation of tines 224 in a proximal direction P (e.g., a direction away from lead body distal end 246).

Here and elsewhere, when a first component is rotationally coupled to a second component, this means a rotation of the first component causes a rotation of the second component. In examples, the rotation of the first component around an axis causes the rotation of the second component around the axis. The rotation of the first component in a particular direction (e.g., clockwise) around the axis may cause the rotation of the second component in the particular direction around the axis. In examples, the rotation of the first component causes the second component to rotate substantially synchronously with the first component.

Torque member 234 is configured to translate laterally (e.g., in a direction parallel to longitudinal axis L) within lumen 238 and relative lead interior surface 236. Additionally, torque member 234 is configured to rotate (e.g., rotate around longitudinal axis L) relative to lead body 218. Torque member 234 may extend from drive shaft 240 through lumen 238 and through an opening (not shown) proximal to lead body distal portion 220, such that a torque may be imparted on torque member 234 from a location outside of lead body distal portion 220. Torque member 234 may be configured to transmit the exerted torque through implantable medical lead 212 to drive shaft 240, in order to effect an extension and/or retraction of tines 224 relative to lead body 218. In examples, torque member 234 is configured such that a clearance C is present between some portion of torque member 234 and lead interior surface 236 to assist in the independent rotation and translation of torque member 234 relative to lead interior surface 236, although this is not required. Torque member 234 may be configured to contact (intentionally or incidentally) lead interior surface 236 over some portion of or substantially all of torque member 234.

Torque member 234 may be mechanically connected to drive shaft 240 in any manner which establishes the rotational coupling between torque member 234 and drive shaft 240. For example, a distal end 242 of torque member 234 ("torque member distal end 242") may be attached to a proximal end 244 of drive shaft 240 ("drive shaft proximal end 244") by welding, soldering, adhesives, pins, or some other suitable fastening method. In some examples, torque member 234 is a torque coil having the form of a helix substantially surrounding a helix interior, and torque member 234 is configured such that, when torque member 234 is rotationally coupled to drive shaft 240, longitudinal axis L passes through at least some portion of the helix interior.

As discussed, torque member 234 is depicted in FIG. 2 as a longitudinal cross-section with a cutting plane parallel to the page. Torque member 234 may have any longitudinal cross-section sufficient to generate the rotational coupling with drive shaft 240. Further, torque member 234 may have any axial cross-section (e.g., a cross-section perpendicular to the longitudinal cross-section) sufficient to generate the rotational coupling with drive shaft 240. The axial cross-section may be circular, oval-shaped, a polygonal, and may include straight and curved segments. The axial cross-section may be substantially solid over substantially all or a portion of the axial cross-section, and may define open areas (e.g. A channel opening) over a portion of the axial cross-section. In examples, torque member 234 may be configured to define a channel 248 ("torque member channel 248") at least partially surrounded by torque member 234. Torque member channel 248 may extend over substantially all or some portion of a length of torque member 234. In examples, torque member 234 defines torque member channel 248 such that longitudinal axis L passes through at least some portion of torque member channel 248.

As will be discussed further, implantable medical lead 212 may include a conductor 249 electrically connected to tines 224 and extending through lumen 238. In examples, conductor 249 extends through torque member channel 248. Conductor 249 may be mechanically coupled to tines 224 or mechanically coupled to a portion of implantable medical lead 212 in electrical communication with tines 224 at a distal end of conductor 249. Conductor 249 may be electrically connected to therapy delivery circuitry (e.g., of IMD 126 (FIG. 1)) at a proximal end of conductor 249. In some examples conductor 249 is configured to rotate when torque member 234 rotates. In other examples, conductor 249 is configured such that torque member 234 rotates relative to conductor 249.

Drive shaft 240 is configured to receive a torque imparted by torque member 234 and rotate (e.g., around longitudinal axis L) in response to the imparted torque. Drive shaft 240 is configured to translate in a direction substantially parallel to longitudinal axis L when torque member 234 rotates drive shaft 240. Drive shaft 240 is configured to rotate relative to lead interior surface 236. In examples, drive shaft 240 is configured to rotate substantially synchronously with torque member 234. Drive shaft 240 may be configured to reside substantially between torque member 234 and tines 224 within lumen 238.

Drive shaft 240 is configured to convert a rotation (e.g., caused by torque member 234) into a lateral translation relative to interior surface 236, with the lateral translation substantially parallel to longitudinal axis L. Drive shaft 240 may convert the rotation into a lateral translation toward a distal end 246 of lead body distal portion 220 ("lead body distal end 246") and/or away from lead body distal end 246. In examples, drive shaft 240 is configured such that rotation of drive shaft 240 in a first direction (e.g. clockwise) around longitudinal axis L generates a lateral translation of drive shaft 240 in a first lateral direction (e.g., the distal direction D), and a rotation of drive shaft 240 in a second direction (e.g., counter-clockwise) opposite the first direction generates a lateral translation of drive shaft 240 in a second lateral direction (e.g., the proximal direction P). Drive shaft 240 is further configured such that the lateral translation laterally translates tines 224, such that tines 224 extend from or retract into lead body 218 when torque member 234 rotates drive shaft 240.

In examples, drive shaft 240 includes a set of external threads 250 ("drive external threads 250") configured to threadably engage lead interior surface 236. Drive external threads 250 are configured to convert the rotation of drive shaft 240 into the lateral translation of drive shaft 240 relative to lead interior surface 236. In examples, drive external threads 250 are configured to threadably engage (e.g., mesh and/or mate with) a set of internal threads 252 on lead interior surface 236 ("surface interior threads 252"). Drive external threads 250 are configured such that, when drive external threads are threadably engaged (e.g., meshed and/or mated) with surface interior threads 252, rotation of drive shaft 240 causes rotation of drive external threads 250, resulting in a lateral translation of drive external threads 250 and drive shaft 240 relative to surface interior threads 252 and lead interior surface 236. Drive shaft 240 may be configured such that drive external threads 250 substantially surround a segment of longitudinal axis L when drive shaft 240 threadably engages interior surface 236. For example, drive external threads 250 may be helical threads surrounding the segment of longitudinal axis L. In some examples, drive external threads 250 may be one or more pins extending radially from drive shaft 240 and configured to fit within a helical slot within lead interior surface 236, and surface interior threads 252 may be the helical slot. In some examples, drive external threads 250 may be a helical slot surrounding drive shaft 240, and surface interior threads 252 may be one or more pins configured to fit into the helical slot.

In examples, drive external threads 250 are formed by an exterior surface 254 of drive shaft 240 ("drive exterior surface 254"). Drive external threads 250 may have a unitary body construction with drive exterior surface 254, such that drive external threads 250 and drive exterior surface 254 are inseparable portions of drive shaft 240. In some examples, drive external threads 250 may comprise a separate thread insert or other component installed around some portion of drive exterior surface 254. Drive internal threads 250 may be any type of thread capable of threadably engaging lead interior surface 236. For example drive internal threads 250 may have any pitch, thread angle, major diameter, and root diameter. Drive internal threads 250 may be configured as V threads, square threads, acme threads, buttress threads, right-handed threads, left-handed threads, and other configurations.

As discussed, drive shaft 240 is depicted in FIG. 2 as a longitudinal cross-section with a cutting plane parallel to the page. Drive shaft 240 may have any longitudinal cross-section sufficient to convert a rotation about longitudinal axis L into a lateral translation of drive shaft 240 substantially parallel to longitudinal axis L. Further, drive shaft 240 may have any axial cross-section sufficient to threadably engage lead interior surface 236. The axial cross-section of drive shaft 240 may be circular, oval-shaped, a polygonal, and may include straight and curved segments. The axial cross-section of drive shaft 240 may be substantially solid over substantially all or a portion of the axial cross-section, and may define open areas. In examples, drive shaft 240 may be configured to define a shaft channel 256 at least partially surrounded by drive shaft 240.

Shaft channel 256, when present, may extend over substantially all or some portion of a length of drive shaft 240 (e.g., a length substantially parallel to longitudinal axis L). In examples, drive shaft 240 defines drive channel 256 such that longitudinal axis L passes through at least some portion of shaft channel 256. In some examples, when torque member 234 is rotationally coupled to drive shaft 240, a distal opening 258 of torque member channel 248 opens into (e.g. Is in fluid communication with) a proximal opening 260 of shaft channel 256. Conductor 249 may extend through some or substantially all of shaft channel 256. In examples, conductor 249 extends through torque member channel 248 and shaft channel 256. In some examples, drive shaft 240 is configured such that drive shaft 240 may rotate relative to conductor 249. In other examples, drive shaft 240 is configured such that conductor 249 rotates when drive shaft 240 rotates.

As discussed, conductor 249 is electrically connected to tines 224 and extends through lumen 238. In examples, conductor 249 extends through torque member channel 248 and/or shaft channel 256. Conductor 249 may be mechanically coupled to tines 224 or mechanically coupled to a portion of implantable medical lead 212 in electrical communication with tines 224. In examples, conductor 249 may be electrically connected to therapy delivery circuitry (e.g., within IMD 126 (FIG. 1)) at a proximal end of conductor 249. IMD 126 may be configured to provide electrical signals, e.g., pacing therapy, through conductor 249 to tines 224, and receive electrical signals, e.g., sensed cardiac electrical signals, through conductor 249 to tines 224.

In some examples, conductor 249 is a multi-conductor comprising a plurality of conductors such as first conductor 261, second conductor 262, and third conductor 263. Each of conductors 261, 262, and 263 may be electrically isolated from at least lead body 218, torque member 234, and drive shaft 240. Further, each individual conductor in the plurality may be electrically isolated from every other individual conductor in the plurality. In examples, each of conductors 261, 262, and 263 is electrically connected to therapy delivery circuitry (e.g., within IMD 126 (FIG. 1)). Each of the conductors 261, 262, and 263 may be configured to receive an individual electrical signal from the therapy delivery circuitry of IMD 126, and transmit the individual electrical signal to tines 224 independently. For example, first conductor 261 may be configured to receive a first electrical signal from the therapy delivery circuitry and provide the first electrical signal to tines 224, second conductor 262 may be configured to receive a second electrical signal from the therapy delivery circuitry and provide the second electrical signal to tines 224, and/or third conductor 263 may be configured to receive a third electrical signal from the therapy delivery circuitry and provide the third electrical signal to tines 224.

In some examples, each of first conductor 261, second conductor 262, and third conductor 263 is electrically connected to an individual tine comprising tines 224. For example, tines 224 may be a plurality of tines including tine 264, tine 265, and tine 266, with each of tines 264, 265, and 266 configured to extend from or retract into lead body 218 as a result of, for example, rotation of drive shaft 240 by torque member 234. Tines 224 may be electrically connected to conductor 249 such that tine 264 is electrically connected to first conductor 261, tine 265 is electrically connected to second conductor 262, and tine 266 is electrically connected to third conductor 263, with each of tines 264, 265, 266 electrically isolated from every other of tines 264, 265, 266. Tine 264 may be configured to receive a first electrical signal from first conductor 261, tine 265 may be configured to receive a second electrical signal from second conductor 262, and/or tine 266 may be configured to receive a third electrical signal from third conductor 263. Hence, implantable medical lead 212 may be configured to provide multi-point stimulation to tissue at or in the vicinity of a target site in a patient (e.g., target site 114 (FIG. 1)). In examples, implantable medical lead 212 is configured to provide multi-point pacing to cardiac tissue within a patient.

As discussed, tines 224 are configured to be extendable and/or retractable with respect to lead body 218, in order to facilitate penetration of tissue in the vicinity of a target site within a patient (e.g., target site 114 (FIG. 1)). The extension and/or retraction of tines 224 may be controlled by a clinician. Lead 212 is configured such that rotation of torque member 234 causes a lateral translation drive shaft 240 and tines 224, extending or retracting tines 224 from lead body 218 (e.g., from lead body distal portion 220).

As used herein, a "tine" refers to an elongated element that extends from a distal end of drive shaft 240. The tine (e.g., one or more of tines 224) may be linear or nonlinear. The tine may be a substantially elastic member (e.g., may tend to return to a zero-stress shape in the absence of externally imparted forces), and may be configured to pierce and potentially penetrate into or through target tissue. In some examples, the tine is configured to function as an electrode. The tine may include a conductor, such as an electrically conductive material, having a non-conductive coating, such as but not limited to polytetrafluoroethylene (PTFE). The tine may be configured such that a portion of the conductive material, e.g., a distal end of the tine, is uncoated by the non-conductive coating, such that the portion of the conductive material is exposed to tissue in which the tine may be embedded (e.g., tissue at or around target site 114 (FIG. 1)). The tine may be formed to have a preset shape and may be formed using any suitable material. In examples, the tine comprises a nickel-titanium alloy such as Nitinol, or other suitable materials.

Implantable medical lead 212 may be configured such that extension and/or retraction of tines 224 occurs over a substantially continuous range, so that a clinician may utilize torque member 234 to establish a particular depth of penetration of tines 224 into the tissue. In examples, therapy delivery circuitry (e.g., within IMD 126) is configured to provide electrical signals to tines 224. In some examples, sensing circuitry is configured to take electrical measurements during penetration of tines 224 into the tissue in order to, for example, determine a suitable depth of penetration of tines 224 within the tissue. In examples, conductor 249 is electrically connected to therapy delivery circuitry, with the therapy delivery circuitry configured to provide electrical signals through conductor 249 to tine 224. Tines 224 may conduct the electrical signals to the target tissue of heart 122 (FIG. 1), causing the cardiac muscle, e.g., of the ventricles, to depolarize and, in turn, contract at a regular interval. In examples in which tines 224 penetrates to a position at or near the HB, RBB, LBB, or other specialized conductive tissue of heart 122, the cardiac pacing delivered via tine 224 may be conduction system pacing (CSP) of heart 122, which may provide more physiologic activation and contraction of heart 122. Tines 224 may also be connected to sensing circuitry of IMD 126 via the conductor, and the sensing circuitry may sense electrical activity of heart 122 via tines 224.

Figure 3:
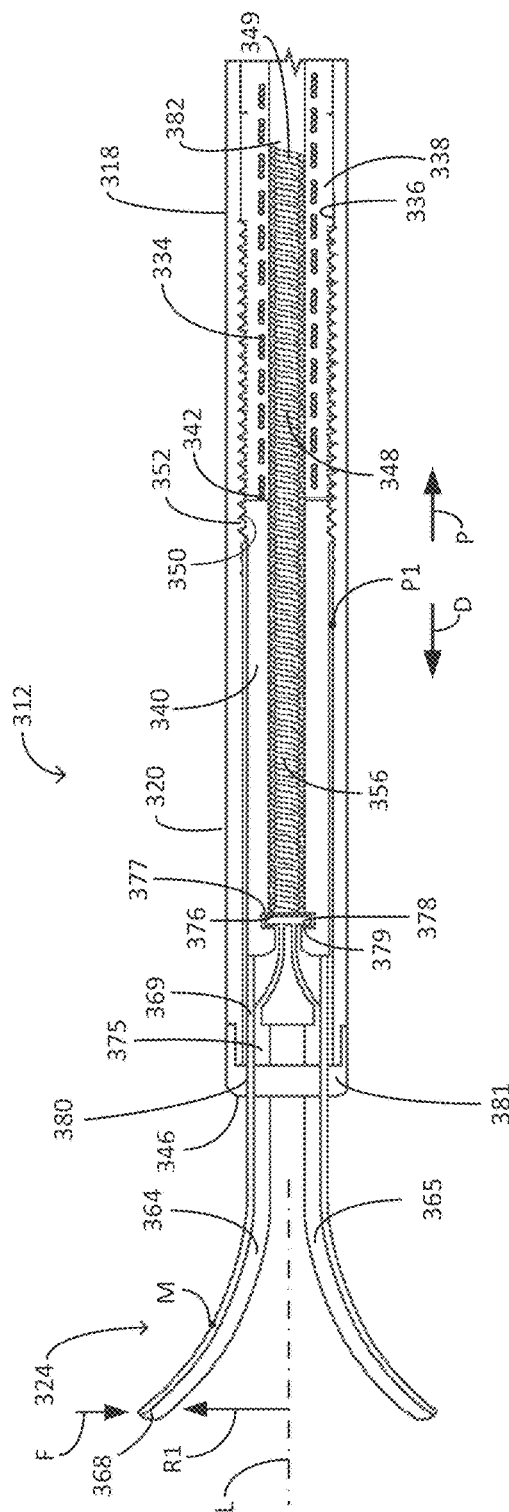
FIG. 3 is a plan view with selected cross-sections illustrating an example implantable medical lead having elongated extendable/retractable tines.

FIG. 3 is a conceptual diagram illustrating a plan view of a portion of an implantable medical lead 312. Implantable medical lead 312 may be an example of implantable medical lead 112 and/or implantable medical lead 212. Implantable medical lead 312 includes lead body 318, lead body distal portion 320, one or more tines 324 ("tines 324"), torque member 334, lead interior surface 336, lumen 338, drive shaft 340, torque member distal end 342, lead body distal end 346, conductor 349, torque member channel 348, drive external threads 350, surface internal threads 352, and shaft channel 356, which may be configured similarly to and operate relative to other implantable medical lead 312 components in the same manner as the like-named components of implantable medical lead 112 and/or implantable medical lead 212, except as otherwise described herein. Lead body 318 defines a longitudinal axis L. FIG. 3 illustrates longitudinal cross-sections of lead body 318, distal portion 320, and torque member 334, with a cutting plane taken parallel to the page.

Implantable medical lead 312 is configured such that tines 324 may extend out of and retract into lead body 318. For example, FIG. 3 illustrates implantable medical lead 312 with tines 324 extending out of lead body 318, such that tines 324 extend distally beyond lead body distal end 346. Torque member 334 is configured to rotate drive shaft 340 around longitudinal axis L and relative to lead interior surface 336. Torque member 334 and drive shaft 340 reside within lumen 338 defined by lead interior surface 336. Drive shaft 340 is configured to convert the rotation around longitudinal axis L into a translation substantially parallel to longitudinal axis L. Drive shaft 340 may convert the rotation into a translation toward lead body distal end 346 or may convert the rotation into a translation away from lead body distal end 346. Drive shaft 340 includes drive external threads 350, which may convert a rotation relative to lead interior surface 336 into a lateral translation relative to lead interior surface 336 through threadable engagement with surface interior threads 352. Drive shaft 340 is configured to impart a lateral force on tines 324 when drive shaft 340 translates substantially parallel to longitudinal axis L, causing tines 324 to translate substantially parallel to longitudinal axis L. Tines 324 are further configured such that, when drive shaft 340 rotates and translates laterally relative to lead interior surface 336, tines 324 translate in the same direction as drive shaft 340.

Tines 324 are configured to remain substantially rotationally stationary with respect to lead interior surface 336 when drive shaft 340 causes tines 324 to translate substantially parallel to longitudinal axis L. For example, tines 324 may be mechanically coupled to a tine support plate 375. FIG. 3 illustrates tine support plate 375 as a longitudinal cross-section with a cutting plane taken parallel to the page. Tine support plate 375 is configured to receive the lateral force imparted by drive shaft 340 as drive shaft translates parallel to longitudinal axis L, and transmit the lateral force to tines 324 in order to cause tines 324 to translate. Tine support plate 375 may transmit the lateral force imparted by drive shaft 340 while maintaining substantially stationary with respect to the rotation of drive shaft 340. For example, tine support plate 375 may include a bearing surface configured to contact drive shaft 340 and receive a lateral force parallel to longitudinal axis L, with the bearing surface configured to be slidable over the contacting portion of drive shaft 340 in a direction perpendicular to longitudinal axis L. Stated similarly, drive shaft 340 may include a thrust surface configured to transmit a force parallel to longitudinal axis L to a bearing surface of tine support plate 375 as the thrust surface slidably rotates over the bearing surface, with a rotation of the thrust surface occurring around the longitudinal axis L.

For example, as depicted in FIG. 3, tine support plate 375 may include a first bearing surface 376 configured to receive a first force from drive shaft 340, with the first force tending to move tine support plate 375 toward lead body distal end 346. Drive shaft 340 includes a first thrust surface 377 configured to transmit the first force to first bearing surface 376. First thrust surface 377 is configured to rotate around longitudinal axis L as first thrust surface 377 imparts the first force to first bearing surface 376. First thrust surface 377 is configured to slidably rotate over (and relative to) first bearing surface 376 when first thrust surface 377 contacts first bearing surface 376 and rotates around longitudinal axis L. Thus, tine support plate 375 may receive the first force as a result of a rotation of drive shaft 340 while remaining substantially rotationally stationary with respect to drive shaft 340. Tine support plate may transmit the first force to tines 324, causing tines 324 to translate parallel to longitudinal axis L while remaining substantially rotationally stationary with respect to drive shaft 340.

Tine support plate 375 may also include a second bearing surface 378 configured to receive a second force from drive shaft 340, with the second force tending to move tine support plate 375 away from lead body distal end 346. Drive shaft 340 includes a second thrust surface 379 configured to transmit the second force to second bearing surface 378. Second thrust surface 379 is configured to rotate around longitudinal axis L as second thrust surface 379 imparts the second force to second bearing surface 378. Second thrust surface 379 is configured to slidably rotate over (and relative to) second bearing surface 378 when second thrust surface 379 contacts second bearing surface 378 and rotates around longitudinal axis L. Thus, tine support plate 375 may receive the second force as a result of a rotation of drive shaft 340 while remaining substantially rotationally stationary with respect to drive shaft 340. Tine support plate may transmit the second force to tines 324, causing tines 324 to translate parallel to longitudinal axis L while remaining substantially rotationally stationary with respect to drive shaft 340.

Consequently, implantable medical lead 312 is configured such that when torque member 334 causes a rotation of drive shaft 340 in a first rotational direction (e.g., clockwise) around longitudinal axis L, drive shaft 340 translates in a first lateral direction (e.g., the distal direction D) and imparts a first force to tine support plate 375. The first force causes tine support plate and tines 324 to move in the first lateral direction while remaining substantially rotationally stationary with respect to drive shaft 340. When torque member 334 causes a rotation of drive shaft 340 in a second rotational direction (e.g., counter-clockwise) around longitudinal axis L, drive shaft 340 translates in a second lateral direction (e.g., the proximal direction P) and imparts a second force to tine support plate 375. The second force causes tine support plate and tines 324 to move in the second lateral direction while remaining substantially rotationally stationary with respect to drive shaft 340. Hence, tines 324 may be extended from lead body distal portion 320 by rotating torque member 334 in the first rotational direction and retracted into lead body distal portion 320 by rotating torque member 334 in the second rotational direction.

Tines 324 may be biased so that at least some portion of tines 324 expands radially as tines 324 extend from lead body distal portion 320. For example, tines 324 include tine 364. Tine 364 is an elongated member having a free end 368 and a fixed end 369, with fixed end 369 at an end of tine 364 opposite free end 368. Fixed end 369 is mechanically coupled to a tine support plate 375. Tine 364 may be biased to drive free end 368 radially outward from longitudinal axis L when fixed end 369 translates in a direction substantially parallel to longitudinal axis L relative to a portion of lead body 318 (e.g., lead interior surface 336). For example, tine 364 may be biased such that a radial distance R1 between free end 368 and longitudinal axis L increases as free end 368 moves in the distal direction D away from a point P1 on lead interior surface 336. Radial distance R1 is perpendicular to the longitudinal axis L and the distal direction D is parallel to the longitudinal axis L. In an example, the biasing of tine 364 results in a tendency of free end 368 to return or attempt to return to an initial position relative to the point P1 when the free end 368 is displaced from the initial position by, for example, a force F acting on free end 368 in the direction shown in FIG. 3. The biasing tending to drive free end 368 radially outward as tine 364 extends from lead body 318 may cause tine 364 to more securely anchor to the tissue of a patient when tine 364 is extended to penetrate the tissue. Tines 324 further include tine 365, which may be configured similarly to tine 364.

Tine 364 defines a midpoint M on tine 364 between free end 368 and fixed end 369. tine 364 may be configured such that the biasing of tine 364 tending to drive free end 368 radially outward causes tine 364 to assume any general shape. In some examples, tine 364 is configured such that the biasing of tine 364 tending to drive free end 368 radially outward tends to cause tine 364 to position such that free end 368 remains distal to midpoint M (e.g., as depicted in FIG. 3). In some examples, tine 364 is configured such that the biasing of tine 364 tending to drive free end 368 radially outward tends to cause tine 364 to position such that free end 368 establishes a position proximal to midpoint M (e.g., a portion of tine 364 forms a general U-shape).

In some examples, tine 364 extends through a tine access 380 of a sleeve head 381. Sleeve head 381 may be located at lead body distal end 346. Sleeve head 381 is configured such that tine access 380 is between fixed end 369 and free end 368 when tine 364 extends through tine access 380. Tine access 380 may circumferentially surrounds some or all of a portion of tine 364. For example, tine access 380 may surround some or all of an axial slice of tine 364 (e.g. A slice of tine 364 bounded by a first cutting plane perpendicular to longitudinal axis L and a second cutting plane perpendicular to longitudinal axis L). Tine access 380 may be configured to guide tine 364 during extension and/or retraction, resist a torque around longitudinal axis L incidentally transferred from drive shaft 340 or tine support plate 375, or some other reason. In some examples, tines 324 comprise a plurality of tines with each tine in the plurality configured to extend out of and retract into lead body 318 (e.g., lead body distal portion 320).

Figure 4:
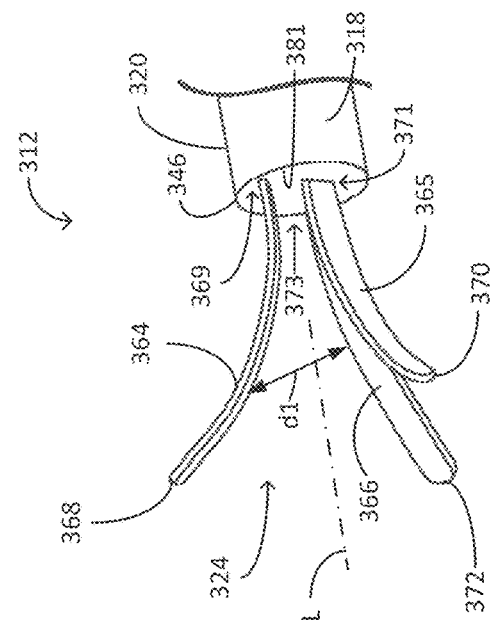
FIG. 4 is a perspective view illustrating a plurality of elongated extendable/retractable tines.

FIG. 4 is a conceptual isometric view of lead body distal portion 320 of implantable medical lead 312. In FIG. 4, implantable medical lead 312 includes plurality of tines 324, with plurality of tines 324 including tines 364, 365, 366. FIG. 4 further illustrates lead body 318, tines 324 including tine 364, tine 365, and tine 366, lead body distal end 346, and sleeve head 381.

Each of tines 364, 365, 366 is an elongated member comprising a fixed end mechanically coupled to some portion of implantable medical lead 312 and a free end opposite the fixed end. For example, tine 364 includes free end 368 and fixed end 369, tine 365 includes free end 370 and fixed end 371, and tine 366 includes free end 372 and fixed end 373. Fixed ends 369, 371, 373 are mechanically coupled to some portion of implantable medical lead 312, such as tine support plate 375 (FIG. 3).

Tine 364 is biased to drive free end 368 radially outward from a longitudinal axis L when tine 364 translates in a direction substantially parallel to longitudinal axis L relative to a portion of lead body 318 (e.g., sleeve head 381). Tines 365, 366 are biased in a similar manner to tine 364 so that, for example, free end 370 drives radially outward from longitudinal axis L when tine 365 translates in a direction substantially parallel to longitudinal axis L, and free end 372 drives radially outward from longitudinal axis L when tine 366 translates in a direction substantially parallel to longitudinal axis L. In examples, each tine (e.g., tine 364) in a plurality of tines is configured to establish its free end (e.g., free end 368) in a position different from a position of any other free end of a tine (e.g., different from free end 370 of tine 365 and free end 372 of tine 366). The differing positions of each of the free ends allows for stimulation of tissue at multiple points when tines 324 penetrate the tissue of a patient.

Individual tines within tines 324 may be configured to be spaced apart from each other in the extended condition. For example, FIG. 4 illustrates tines 364 and tine 365 spaced apart from each other by a distance d1. Distance d1 may be expressed as a linear distance over a line oriented perpendicular to longitudinal axis L, and may be between any portion of tine 364 and any portion of tine 365 (e.g., may be between fixed end 369 and fixed end 371, between free end 368 and free and 370, or between other portions of tine 364 and tine 365). The distance d1 may also be expressed as an angle having a vertex on longitudinal axis L. In some examples, distance d1 may be in the range of 30 to 180 degrees. The illustrated number and arrangement of tines 324 is one non-limiting example, and implantable medical lead 312 may, in other examples, include a different number of individual tines comprising tines 324 and/or a different positions of one or more individual tines comprising tines 324. In an example, tines 324 may include a plurality of tines substantially equally distributed circumferentially around longitudinal axis L.

Returning to FIG. 3, implantable medical lead 312 includes conductor 349 extending within torque member channel 348 of torque member 334. Conductor 349 may further extend through substantially all or some portion of shaft channel 356. Conductor 349 may be a multi-conductor comprising a plurality of conductors. Conductor 349 may be configured such that each individual conductor in the plurality of conductors is electrically connected to an individual tine in a plurality of tines (e.g., connected to tine 364, tine 365, or tine 366 (FIG. 4)). In examples, conductor 349 is configured such that each individual conductor is electrically connected to therapy delivery circuitry (e.g., within IMD 126 (FIG. 1)). The individual conductor may be configured to receive an individual electrical signal from the therapy delivery circuitry and transmit the individual electrical signal to the individual tine. For example, a first individual conductor within conductor 349 may be configured to receive a first electrical signal from the therapy delivery circuitry and provide the first electrical signal to tine 364, a second individual conductor within conductor 349 may be configured to receive a second electrical signal from the therapy delivery circuitry and provide the second electrical signal to tine 365, a third individual conductor within conductor 349 may be configured to receive a third electrical signal from the therapy delivery circuitry and provide the third electrical signal to tine 366, and so on. Hence, implantable medical lead 312 may be configured to provide multipoint stimulation to tissue at or in the vicinity of a target site in a patient (e.g., target site 114 (FIG. 1)). In examples, implantable medical lead 312 is configured to provide multi-point pacing to cardiac tissue within a patient. Conductor 349 may include an insulative jacket 382 around all or some portion of conductor 349. Insulative jacket 382 may electrically isolate conductor 349 from other portions of implantable medical lead 312.

Figure 5:
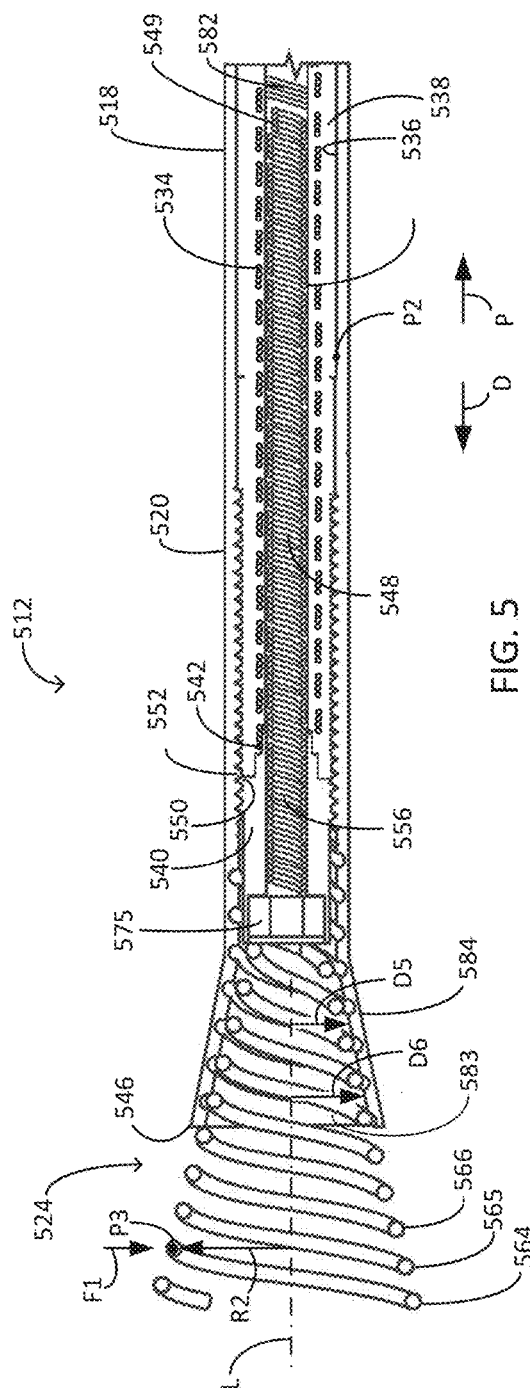
FIG. 5 is a plan view with selected cross-sections illustrating an example implantable medical lead having helical extendable/retractable tines.

FIG. 5 is a conceptual diagram illustrating a plan view of a portion of an example implantable medical lead 512. Implantable medical lead 512 may be an example of implantable medical lead 112 and/or implantable medical lead 212. Implantable medical lead 512 includes lead body 518, lead body distal portion 520, one or more tines 524 ("tines 524") including tine 564, tine 565, and tine 566, torque member 534, lead interior surface 536, lumen 538, drive shaft 540, torque member distal end 542, lead body distal end 546, conductor 549, torque member channel 548, drive external threads 550, surface internal threads 552, shaft channel 556, tine support plate 575, and insulative jacket 582, which may be configured similarly to and operate relative to other implantable medical lead 512 components in the same manner as the like-named components of implantable medical lead 112, implantable medical lead 212, and/or implantable medical lead 312, except as otherwise described herein. Lead body 518 defines a longitudinal axis L. FIG. 5 illustrates longitudinal cross-sections of lead body 518, distal portion 520, and torque member 534, conductor 549, tine 564, tine 565, and tine 566, with a cutting plane taken parallel to the page.

Figure 6:
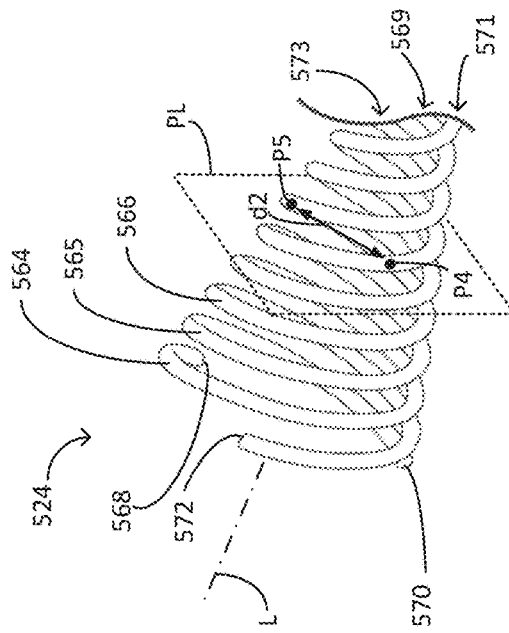
FIG. 6 is a perspective view illustrating a plurality of helical extendable/retractable tines.

FIG. 6 is a conceptual isometric view of tines 524, where tines 524 comprise a plurality of tines. FIG. 6 illustrates tines 524 including tine 564 having free end 568 and fixed end 569, tine 565 having free end 570 and fixed end 571, and tine 566 having free end 572 and fixed end 573. Tines 524 may include only a single tine, such as tine 564, or may include a plurality of tines, such as tine 564, tine 565, tine 566, and others.

Implantable medical lead 512 is configured such that tines 524 extend out of and retract into lead body 518 as a helix (e.g., a helical coil) surrounding longitudinal axis L. When tines 524 comprise a plurality of tines, each tine in the plurality may form a helix surrounding longitudinal axis L. One or more of tines may be a helix substantially symmetric around longitudinal axis L. Tines 524 are rotationally coupled (e.g., via tine support plate 575) to drive shaft 540 and configured to rotate around longitudinal axis L when drive shaft 540 rotates around longitudinal axis L. Implantable medical lead 512 may be configured such that when drive shaft 540 rotates in a first direction (e.g., clockwise) around longitudinal axis L, tines 524 rotate in the first direction around longitudinal axis L, and when drive shaft 540 rotates in a second direction (e.g., counter-clockwise) around longitudinal axis L, tines 524 rotate in the second direction around longitudinal axis L. In examples, tines 524 are configured to rotate substantially synchronously with drive shaft 540.

Torque member 534 is configured to rotate drive shaft 540 around longitudinal axis L and relative to lead interior surface 536. Torque member 534 and drive shaft 540 reside within lumen 538 defined by lead interior surface 536. Drive shaft 540 is configured to convert the rotation around longitudinal axis L into a translation substantially parallel to longitudinal axis L. Drive shaft 540 may convert the rotation into a translation in the distal direction D (e.g., toward lead body distal end 546) and may convert the rotation into a translation in the proximal direction P (e.g., away from lead body distal end 546). Drive shaft 540 includes drive external threads 550, which may convert a rotation relative to lead interior surface 536 into a lateral translation relative to lead interior surface 536 through threadable engagement with surface interior threads 552. Drive shaft 540 is configured to impart a lateral force on tines 524 when drive shaft 540 translates substantially parallel to longitudinal axis L, causing tines 524 to translate substantially parallel to longitudinal axis L. Tines 524 are further configured such that, when drive shaft 540 rotates and translates laterally relative to lead interior surface 536, tines 524 translate in the same direction as drive shaft 540.

Figure 7:
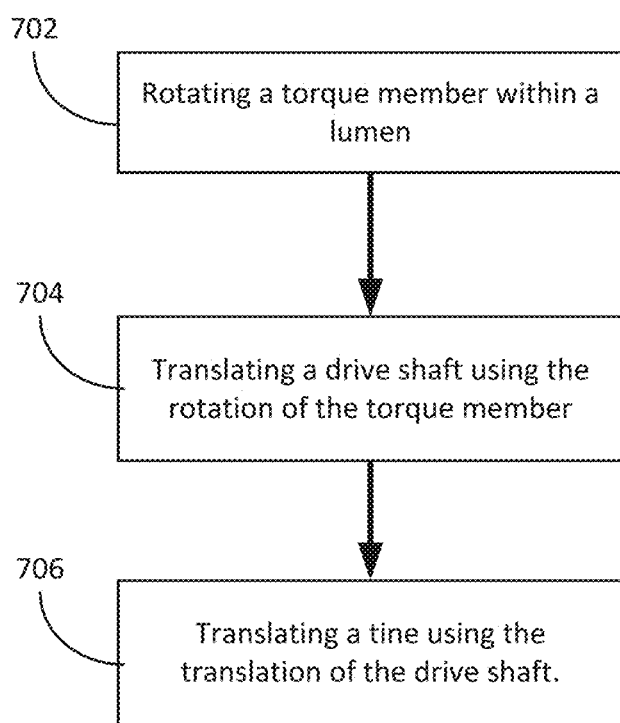
FIG. 7 illustrates an example technique for extending an example tine from an example implantable medical lead.

Individual tines (e.g., tine 564, tine 565, and/or tine 566) within tines 524 may be configured to be spaced apart from each other in the extended condition. For example, FIG. 7 illustrates tine 565 and tine 566 spaced apart from each other by a distance d2. Distance d2 may expressed as a linear distance over a line between a point P4 and a point P5, where point P4 is an intersection of some portion of tine 565 onto a plane PL perpendicular to longitudinal axis L, and point P5 an intersection of some portion of tine 566 onto the plane PL. The distance d2 may also be expressed as an angle having a vertex on longitudinal axis L. In some examples, distance d2 may be in the range of 30 to 180 degrees. The illustrated number and arrangement of tines 524 is one non-limiting example, and implantable medical lead 512 may, in other examples, include a different number of individual tines comprising tines 524 and/or a different positions of one or more individual tines comprising tines 524. In an example, tines 524 may include a plurality of tines substantially equally distributed circumferentially around longitudinal axis L.

In some examples, each individual tine (e.g., tine 564) in a plurality of tines is configured to establish its free end (e.g., free end 568) in a position different from a position of any other free end of a tine (e.g., different from free end 570 of tine 565 and free end 572 of tine 566). The differing positions of each of the free ends allows for stimulation of tissue at multiple points when tines 524 penetrate the tissue of a patient.

Tines 524 are further configured to be rotationally coupled with drive shaft 540 such that tines 524 rotate with respect to lead interior surface 336 when drive shaft 540 rotates with respect to lead interior surface 536. Consequently, when drive shaft 540 rotates to cause tines 524 to laterally translate substantially parallel to longitudinal axis L, tines 524 also rotate around longitudinal axis L during the lateral translation. For example, tines 524 may be mechanically coupled to a tine support plate 575, with tine support plate 575 configured to rotate when drive shaft 540 rotates. Tine support plate 575 is configured to receive a lateral force imparted by drive shaft 540 as drive shaft translates parallel to longitudinal axis L, as well as receive a rotational torque from drive shaft 540 as drive shaft 540 rotates around longitudinal axis L. Tine support plate 575 transmits the lateral force and the rotational torque to tines 524, in order cause tines 524 to translate parallel to longitudinal axis L while rotating about longitudinal axis L.

Tine support plate 575 may be configured to contact tines 524 in any manner sufficient to transfer a torque around longitudinal axis L from drive shaft 540 to tines 524. In some examples, tine support plate 575 is attached to tines 524 (e.g., fixed end 569, fixed end 571, and/or fixed end 573 (FIG. 6)) by welding, soldering, adhesives, pins, or some other suitable fastening method. Further, tine support plate 575 may be configured to contact drive shaft 540 in any manner sufficient to receive a torque around longitudinal axis L from drive shaft 540. In some examples, tine support plate 575 may be a separate component installed on some portion of drive shaft 540 by welding, soldering, adhesives, pins, or some other suitable fastening method. In some examples, tine support plate 575 has a unitary body construction with drive shaft 540, such that tine support plate 575 and drive shaft 540 are inseparable portions of drive shaft 540.

Consequently, implantable medical lead 512 is configured such that when torque member 534 causes a rotation of drive shaft 540 in a first rotational direction (e.g., clockwise) around longitudinal axis L, drive shaft 540 translates in a first lateral direction (e.g., in the distal direction D) and imparts a first rotational torque and a first force to tine support plate 575. The first force causes tine support plate 575 and tines 524 to move in the first lateral direction while rotating in the first rotational direction around longitudinal axis L. When torque member 534 causes a rotation of drive shaft 540 in a second rotational direction (e.g., counter-clockwise) around longitudinal axis L, drive shaft 540 translates in a second lateral direction (e.g., the proximal direction P) and imparts a second rotational torque and a second force to tine support plate 575. The second force causes tine support plate 575 and tines 524 to move in the second lateral direction while rotating in the second rotational direction around longitudinal axis L. Hence, tines 524 may be extended while rotating from lead body distal portion 520 by rotating torque member 534 in the first rotational direction, and retracted while rotating into lead body distal portion 520 by rotating torque member 534 in the second rotational direction.

Tines 524 may be biased so that at least some portion of tines 524 expands radially as tines 524 extend from lead body distal portion 520. For example, tines 524 include tine 564 configured as a helix. A fixed end of tine 564 is mechanically coupled to tine support plate 575. Tine 564 may be biased to drive a point on tine 564 (e.g., point P3) radially outward from longitudinal axis L when tine 564 translates in a direction substantially parallel to longitudinal axis L relative to a portion of lead body 518 (e.g., lead interior surface 536). For example, tine 564 may be biased such that a radial distance R2 between point P3 and longitudinal axis L increases as tine 564 moves in the distal direction D away from a point P2 on lead interior surface 536. Radial distance R2 is perpendicular to the longitudinal axis L and the distal direction D is parallel to the longitudinal axis L. In an example, the biasing of tine 564 results in a tendency of point P3 to return or attempt to return to an initial position relative to the point P2 when the point P3 is displaced from the initial position by, for example, a force F1 acting on tine 564 in the direction shown in FIG. 5. The biasing tending to drive point P3 radially outward as tine 564 extends from lead body 518 may cause tine 564 to more securely anchor to the tissue of a patient when tine 564 is extended and rotated during penetration of the tissue. Tine 565, tine 566, and any other tines within tines 524 may be biased in a similar manner to tine 564.

Tines 524 may be configured so that some portion of tines 524 contract radially as tines 524 are retracted into lead body distal portion 520. For example, tine 564 may be configured to radially compress such that the radial distance R2 between point P3 and longitudinal axis L decreases as tine 564 moves in the proximal direction P relative to the point P2 on lead interior surface 536. The biasing tending to drive point P3 radially inward as tine 564 retracts into lead body 518 allows implantable medical lead 512 to establish a more compact configuration if, for example, tines 524 are retracted to unanchor implantable medical lead 512 and retrieve or reposition implantable medical lead 512.

Lead interior surface 536 defines a distal opening 583 at a lead body distal end 546 ("lead distal opening 583"). Lead distal opening 583 is configured to allow passage of tines 524 through lead distal opening 583 as drive shaft 540 acts to extend and/or retract tines 524 through lead distal opening 583. In examples, lead body distal portion 520 includes an expanding section 584 configured to flare radially outwards (e.g., conically outwards). Expanding section 584 may comprise a funnel shape substantially centered around longitudinal axis L. In examples, expanding section 584 defines a distance D5 and a distance D6 between lead interior surface 536 and longitudinal axis L, with the distance D5 located proximal to the distance D6, and with the distance D5 less than the distance D6. The distance D5 and the distance D6 may be perpendicular to the longitudinal axis L. Tines 524 may be configured to contact expanding section 584 as tines 524 extend and/or retract from lead body 518.

In some examples, expanding section 584 includes a groove 586 configured to guide one or more of tines 524 during extension and/or retraction. Groove 586 may be configured to at least partially surround a circumference of one or more of tines 564, 565, 566 as tines 564, 565, 566 laterally translate through expanding section 584 (e.g., during extension and/or retraction). Groove 586 may substantially surround longitudinal axis L in order to guide some portion of tines 524 as tines 524 rotate while extending and/or retracting. Lead interior surface 536 may define groove 586. In examples, lead interior surface 536 defines a portion of groove 586 in a section of lumen 238 having a substantially constant radius from longitudinal axis L. For example, some portion of groove 586 may be defined by lead interior surface 536 as a substantially constant spiral groove distal to surface internal threads 552.

Implantable medical lead 512 includes conductor 549 extending within torque member channel 548 of torque member 534. Conductor 549 may further extend through substantially all or some portion of shaft channel 556. Conductor 549 is configured to be rotationally coupled with drive shaft 540. In examples, when torque member 534 causes a rotation of drive shaft 540 in a first direction around longitudinal axis L (e.g., clockwise), conductor 549 rotates in the first direction around longitudinal axis L. When torque member 534 causes a rotation of drive shaft 540 in a second direction around longitudinal axis L (e.g., counter-clockwise), conductor 549 may rotate in the second direction around longitudinal axis L. Conductor 549 may be attached to drive shaft 540 and/or tine support plate 575 in order to, for example, establish a rotational coupling with drive shaft 540. Conductor may be attached to drive shaft 540 and/or tine support plate 575 by welding, soldering, adhesives, pins, or some other suitable fastening method.

Conductor 549 may be a multi-conductor comprising a plurality of conductors. Conductor 549 may be configured such that each individual conductor in the plurality of conductors is electrically connected to an individual tine in a plurality of tines (e.g., connected to tine 564, tine 565, or tine 566. In examples, conductor 549 is configured such that each individual conductor is electrically connected to therapy delivery circuitry (e.g., within IMD 126 (FIG. 1)). The individual conductor may be configured to receive an individual electrical signal from the therapy delivery circuitry and transmit the individual electrical signal to the individual tine. For example, a first individual conductor within conductor 549 may be configured to receive a first electrical signal from the therapy delivery circuitry and provide the first electrical signal to tine 564, a second individual conductor within conductor 549 may be configured to receive a second electrical signal from the therapy delivery circuitry and provide the second electrical signal to tine 565, a third individual conductor within conductor 549 may be configured to receive a third electrical signal from the therapy delivery circuitry and provide the third electrical signal to tine 566, and so on. Hence, implantable medical lead 512 may be configured to provide multi-point stimulation to tissue at or in the vicinity of a target site in a patient (e.g., target site 114 (FIG. 1)). In examples, implantable medical lead 512 is configured to provide multi-point pacing to cardiac tissue within a patient.

A technique for inserting one or more tines into the tissue at or near a target site 114 of a patient 116 is illustrated in FIG. 7. The technique includes rotating a torque member 234, 334, 534 around a longitudinal axis L within a lumen 238, 338, 538 defined by a lead interior surface 236, 336, 536 of a lead body 118, 218, 318, 518 (702). The technique may include rotating the torque member 234, 334, 534 relative to the lead interior surface 236, 336, 536. The technique further includes rotating a drive shaft 240, 340, 540 using the rotation of the torque member 234, 334, 534 (704). The technique may include rotating the drive shaft 240, 340, 540 relative to the lead interior surface 236, 336, 536. The technique may include rotating a set of drive external threads 250, 350, 550 coupled to drive shaft 240, 340, 540 using the rotation of the drive shaft 240, 340, 540.

The technique includes threadably engaging drive shaft 240, 340, 540 and lead interior surface 236, 336, 536. Threadably engaging drive shaft 240, 340, 540 and lead interior surface 236, 336, 536 may include threadably engaging the set of drive external threads 250, 350, 550 with a set of surface interior threads 252, 352, 552 on lead interior surface 236, 336, 536. The technique further includes converting the rotation of the drive shaft 240, 340, 540 into a lateral translation of drive shaft 240, 340, 540 using the threaded engagement. The technique may include laterally translating the drive shaft 240, 340, 540 relative to the lead interior surface 236, 336, 536.

The technique includes translating one or more tines 124, 224, 324, 524 using the lateral translation of drive shaft 240, 340, 540 (706). The technique may include extending tines 124, 224, 324, 524 from the lead body 118 using the lateral translation of drive shaft 240, 340, 540. In examples, the technique includes retracting tines 124, 224, 324, 524 into the lead body 118 using the lateral translation of drive shaft 240, 340, 540. In some examples, the technique includes extending tines 124, 224, 324, 524 from the lead body 118, 218, 318, 518 by rotating drive shaft 240, 340, 540 in a first direction (e.g., clockwise) around the longitudinal axis L and retracting tines 124, 224, 324, 524 into the lead body 118, 218, 318, 518 by rotating drive shaft 240, 340, 540 in a second direction (e.g., counter-clockwise) around the longitudinal axis L. The technique may include displacing some portion of tines 124, 224, 324, 524 radially outward from the longitudinal axis L while extending tines 124, 224, 324, 524 and may include displacing some portion of tines 124, 224, 324, 524 radially inward toward the longitudinal axis L while retracting tines 124, 224, 324, 524.

The technique may include transmitting an electrical signal over a conductor 249, 349, 549 to one or more of tines 124, 224, 324, 524. The technique may include transmitting the electrical signal over individual conductors comprising the conductor 249, 349, 549. The technique may include transmitting a first electrical signal to a first tine 264, 364, 564 using a first conductor of the conductor 249, 349, 549, transmitting a second electrical signal to a second tine 265, 365, 565 using a second conductor of the conductor 249, 349, 549, and/or transmitting a third electrical signal to a third tine 266, 366, 566 using a third conductor of the conductor 249, 349, 549. The technique may include generating the first electrical signal, the second electrical signal, and/or the third electrical signal using therapy delivery circuitry electrically connected to the conductor 249, 349, 549.

The technique may include laterally translating conductor 249, 349, 549 within lumen 238, 338, 538. The technique may include laterally translating conductor 249, 349, 549 within a torque member channel 248, 348, 548.

The technique may include rotating drive shaft 240, 340, 540 relative to tines 124, 224, 324 (e.g., maintaining tines 124, 224, 324 substantially stationary with respect to lead interior surface 236, 336). The technique may include rotating drive shaft 240, 340 relative to conductor 249, 349 (e.g., maintaining conductor 249, 349 substantially rotationally stationary with respect to lead interior surface 236, 336). The technique may include rotating tines 124, 224, 524 using the rotation of drive shaft 240, 540 (e.g., rotating tines 124, 224, 524 relative to lead interior surface 236, 536). The technique may include rotating conductor 249, 549 using the rotation of drive shaft 240, 540 (e.g., rotating conductor 249, 549 relative to lead interior surface 236, 536).

The disclosure includes the following examples.

Example 1: An implantable medical lead comprising; a lead body comprising an interior surface defining a lumen, wherein the lead body defines a longitudinal axis; a drive shaft configured to threadably engage the interior surface; a torque member configured to rotate the drive shaft around the longitudinal axis, wherein the drive shaft is configured to translate in a direction substantially parallel to the longitudinal axis when the torque member rotates the drive shaft; and one or more tines, wherein the one or more tines are configured to at least partially extend out of the lead body when the torque member rotates the drive shaft in a first direction and at least partially retract into the lumen when the torque member rotates the drive shaft in a second direction, and wherein the lumen is sized to allow passage of the torque member and at least a portion of the drive shaft therethrough.

Example 2: The implantable medical lead of example 1, wherein the drive shaft is configured to translate the one or more tines in the direction substantially parallel to the longitudinal axis when the drive shaft translates in the direction substantially parallel to the longitudinal axis.

Example 3: The implantable medical lead of example 1 or example 2, wherein the one or more tines is a plurality of tines, wherein each tine comprises a fixed end attached to the implantable medical lead and comprises a free end, wherein each tine is configured to establish a position of the free end different from a position of every other free end when the plurality of tines at least partially extends out of the lead body.

Example 4: The implantable medical lead of any of examples 1-3, wherein the torque member comprises a torque coil.

Example 5: The implantable medical lead of any of examples 1-4, wherein the torque member is configured to rotate relative to the interior surface when the torque member rotates the drive shaft.

Example 6: The implantable medical lead of any of examples 1-5, wherein the drive shaft is configured to rotate relative to the interior surface when the torque member rotates the drive shaft.

Example 7: The implantable medical lead of any of examples 1-6, wherein the drive shaft is configured to translate in the direction substantially parallel to the longitudinal axis relative to the interior surface.

Example 8: The implantable medical lead of any of examples 1-7, wherein the lumen defined by the interior surface surrounds the longitudinal axis defined by the lead body.

Example 9: The implantable medical lead any of examples 1-8, further comprising a conductor coupled to the one or more tines and configured to extend through the lumen.

Example 10: The implantable medical lead of example 9, wherein: the one or more tines is a plurality of tines, each tine in the plurality of tines is in electrical communication with the conductor, and each tine in the plurality of tines is electrically isolated from every other tine in the plurality of tines.

Example 11: The implantable medical lead of example 10, wherein the conductor is a multi-conductor comprising a plurality of conductors, and wherein each tine is in electrical communication with at least one of the conductors in the plurality of conductors.

Example 12: The implantable medical lead of any of examples 9-11, wherein the torque member defines a channel, and wherein the conductor passes through the channel.

Example 13: The implantable medical lead of example 12, wherein the torque member surrounds the channel and defines a distal opening of the channel at a distal end of the channel and a proximal opening of the channel at a proximal end of the channel, wherein the torque member is sized to allow passage of the conductor through the distal end and the proximal end.

Example 14: The implantable medical lead any of examples 1-13, wherein the lumen defines a proximal opening of the lead body in a proximal portion of the lead body, and wherein the drive shaft is configured to threadably engage with the interior surface of the lumen in a distal portion of the lead body.

Example 15: The implantable medical lead of example 14, wherein the torque member is configured to extend from the drive shaft to the proximal opening of the lead body.

Example 16: The implantable medical lead any of examples 1-15, wherein the drive shaft is configured to rotate relative to the interior surface and relative to the one or more tines when the torque member rotates the drive shaft.

Example 17: The implantable medical lead any of examples 1-15, wherein: the drive shaft is configured to rotate relative to the interior surface when the torque member rotates the drive shaft, and the one or more tines are rotationally coupled with the drive shaft.

Example 18: The implantable medical lead any of examples 1-17, wherein the drive shaft is between the one or more tines and the torque member.

Example 19: An implantable medical lead comprising: a lead body comprising an interior surface defining a lumen, wherein the lead body defines a longitudinal axis; a drive shaft configured to threadably engage with the interior surface; a torque member configured to rotate the drive shaft around the longitudinal axis, wherein: the drive shaft is configured to translate in a direction substantially parallel to the longitudinal axis when the torque member rotates the drive shaft, and the drive shaft is configured to rotate relative to the interior surface when the torque member rotates the drive shaft; and one or more tines, wherein: the one or more tines are configured to at least partially extend out of the lead body when the torque member rotates the drive shaft in a first direction and at least partially retract into the lumen when the torque member rotates the drive shaft in a second direction, the drive shaft is configured to rotate relative to the one or more tines when the torque member rotates the drive shaft, and the lumen is sized to allow passage of the torque member and at least a portion of the drive shaft therethrough.

Example 20: The implantable medical lead of example 19, wherein the drive shaft is configured to translate the one or more tines in the direction substantially parallel to the longitudinal axis when the drive shaft translates in the direction substantially parallel to the longitudinal axis.

Example 21: The implantable medical lead of example 19 or example 20, wherein the one or more tines is a plurality of tines, wherein each tine comprises a fixed end attached to the implantable medical lead and comprises a free end, wherein each tine is configured to establish a position of the free end different from a position of every other free end when the plurality of tines at least partially extends out of the lead body.

Example 22: The implantable medical lead any of examples 19-21, wherein the drive shaft is between the one or more tines and the torque member.

Example 23: The implantable medical lead any of examples 19-22, wherein the one or more tines includes a fixed end and a free end, wherein the fixed end is mechanically coupled to the drive shaft, and wherein the tine is biased to drive the free end radially outward from the longitudinal axis when the tine translates in the direction substantially parallel to the longitudinal axis relative to the interior surface.

Example 24: The implantable medical lead of any of examples 19-23, wherein: the drive shaft is configured to translate in the direction substantially parallel to the longitudinal axis relative to the interior surface, and the drive shaft is configured to translate the one or more tines in the direction substantially parallel to the longitudinal axis when the drive shaft translates in the direction substantially parallel to the longitudinal axis.

Example 25: The implantable medical lead any of examples 19-24, wherein the torque member is configured to rotate relative to the interior surface when the torque member rotates the drive shaft around the longitudinal axis.

Example 26: The implantable medical lead any of examples 19-25, further comprising a conductor coupled to the one or more tines and configured to extend through the lumen.

Example 27: The implantable medical lead of example 26, wherein: the one or more tines is a plurality of tines, each tine in the plurality of tines is in electrical communication with the conductor, and each tine in the plurality of tines is electrically isolated from every other tine in the plurality of tines.

Example 28: The implantable medical lead of example 27, wherein the conductor is a multi-conductor comprising a plurality of conductors, and wherein each tine is in electrical communication with at least one of the conductors in the plurality of conductors.

Example 29: The implantable medical lead of example 27 or example 28, wherein the drive shaft is configured to rotate relative to the conductor when the torque member rotates the drive shaft.

Example 30: The implantable medical lead any of examples 27-29, wherein the torque member defines a channel, and wherein the torque member is sized to allow passage of the conductor through the channel.

Example 31: The implantable medical lead of example 30, wherein the torque member surrounds the channel and defines a distal opening of the channel at a distal end of the channel and a proximal opening of the channel at a proximal end of the channel, wherein the torque member is sized to allow passage of the conductor through the distal end and the proximal end.

Example 32: The implantable medical lead any of examples 19-31, wherein the torque member is a torque coil.

Example 33: The implantable medical lead any of examples 19-32, wherein the drive shaft is configured to translate in a direction substantially parallel to the longitudinal axis when the torque member transmits the torque to the drive shaft.

Example 34: The implantable medical lead any of examples 19-33, wherein the lead body comprises a sleeve head configured to allow passage of the tine through the sleeve head.

Example 35: An implantable medical lead comprising: a lead body comprising an interior surface defining a lumen, wherein the lead body defines a longitudinal axis; a drive shaft configured to threadably engage the interior surface; a torque member configured to rotate the drive shaft around the longitudinal axis, wherein: the drive shaft is configured to translate in a direction substantially parallel to the longitudinal axis when the torque member rotates the drive shaft, and the drive shaft is configured to rotate relative to the interior surface when the torque member rotates the drive shaft; and one or more tines, wherein: the one or more tines are configured to at least partially extend out of the lead body when the torque member rotates the drive shaft in a first direction and at least partially retract into the lumen when the torque member rotates the drive shaft in a second direction, and the one or more tines are rotationally coupled with the drive shaft.

Example 36: The implantable medical lead of example 35, wherein the drive shaft is configured to translate the one or more tines in the direction substantially parallel to the longitudinal axis when the drive shaft translates in the direction substantially parallel to the longitudinal axis.

Example 37: The implantable medical lead of example 35 or example 36, wherein the one or more tines is a plurality of tines, wherein each tine comprises a fixed end attached to the implantable medical lead and comprises a free end, wherein each tine is configured to establish a position of the free end different from a position of every other free end when the plurality of tines at least partially extends out of the lead body.

Example 38: The implantable medical lead any of examples 35-37, wherein the one or more tines includes a helical coil having a fixed end and a free end, wherein the fixed end is rotationally coupled to the drive shaft.

Example 39: The implantable medical lead of any of examples 35-38, wherein the drive shaft is between the one or more tines and the torque member.

Example 40: The implantable medical lead of example 39, wherein: the drive shaft is configured to translate in a direction substantially parallel to the longitudinal axis relative to the interior surface of the lumen when the torque member rotates the drive shaft, and the drive shaft is configured to translate the one or more tines in the direction substantially parallel to the longitudinal axis when the drive shaft translates in the direction substantially parallel to the longitudinal axis.

Example 41: The implantable medical lead of example 39 or example 40, wherein the lead body defines a distal opening of the lumen, wherein the distal opening is configured to allow passage of the one or more tines through the distal opening.

Example 42: The implantable medical lead of example 41, wherein the lead body defines an expanding section of the lumen adjacent the distal opening, wherein the expanding section is configured to flare radially outwards from the longitudinal axis.

Example 43: The implantable medical lead of example 41 or example 42, wherein the one or more tines include a helical coil configured to expand radially outward from the longitudinal axis when the helical coil translates through the distal opening in a direction from a proximal end of the lead body and toward the distal opening.

Example 44: The implantable medical lead any of examples 41-43, wherein the one or more tines include a helical coil configured to contract radially inward toward the longitudinal axis when the helical coil translates through the distal opening in a direction from the distal opening and toward a proximal end of the lead body.

Example 45: The implantable medical lead any of examples 41-44, wherein the one or more tines include a helical coil, and wherein the lead body defines a groove in the interior surface, wherein the groove is configured to guide the helical coil toward the distal opening.

Example 46: The implantable medical lead any of examples 35-45, further comprising a conductor coupled to the one or more tines and configured to extend through the lumen.

Example 47: The implantable medical lead of example 46, wherein: the one or more tines is a plurality of tines, each tine in the plurality of tines is in electrical communication with the conductor, and each tine in the plurality of tines is electrically isolated from every other tine in the plurality of tines.

Example 48: The implantable medical lead of example 47, wherein the conductor is a multi-conductor comprising a plurality of conductors, and wherein each tine is in electrical communication with at least one of the conductors in the plurality of conductors.

Example 49: The implantable medical lead any of examples 46-48, wherein the conductor is rotationally coupled with the drive shaft.

Example 50: The implantable medical lead any of examples 46-49, wherein the torque member defines a channel, and wherein the torque member is sized to allow passage of the conductor through the channel.

Example 51: The implantable medical lead any of examples 35-50, wherein the one or more tines is a plurality of tines, and wherein each tine in the plurality of tines is a helical coil.

Example 52: The implantable medical lead of example 51, wherein each helical coil in the plurality of tines is substantially symmetric around the longitudinal axis.

Example 53: The implantable medical lead any of examples 35-52, wherein the torque member is a torque coil.

Example 54: The implantable medical lead any of examples 35-53, wherein the torque member is configured to rotate relative to the interior surface when the torque member rotates the drive shaft.

Example 55: A method of inserting one or more tines comprising: rotating a torque member within a lumen of lead body around a longitudinal axis, wherein an interior surface of the lead body defines the lumen; rotating a drive shaft rotationally coupled to the torque member using the rotation of the torque member; threadably engaging the drive shaft and the interior surface; converting the rotation of the drive shaft into a lateral translation of the drive shaft using the threaded engagement; and extending one or more tines from the lead body by translating the one or more tines using the lateral translation of the drive shaft.

Example 56: The method of example 55, wherein converting the rotation of the drive shaft comprises rotating a set of external threads on the drive shaft using the rotation of the drive shaft.

Example 57: The method of example 55 or example 56, wherein threadably engaging the drive shaft and the interior surface comprises threadably engaging the drive shaft and a set of internal threads on the interior surface.

Example 58: The method any of examples 55-57, further comprising rotating the torque member relative to the interior surface.

Example 59: The method any of examples 55-58, further comprising laterally translating the drive shaft relative to the interior surface.

Example 60: The method any of examples 55-59, further comprising rotating the drive shaft relative to the one or more tines.

Example 61: The method any of examples 55-60, further comprising rotating the one or more tines using the rotation of the drive shaft.

Example 62: The method any of examples 55-61, further comprising extending the one or more tines by translating a fixed end of the tine.

Example 63: The method any of examples 55-62, further comprising displacing a free end of the one or more tines radially outward from the longitudinal axis.

Example 64: The method any of examples 55-63, further comprising transmitting an electrical signal to the one or more tines using a conductor within the lumen.

Example 65: The method any of examples 55-64, further comprising rotating the drive shaft relative to the conductor.

Example 66: The method any of examples 55-65, further comprising rotating the conductor while rotating the torque member.

Example 67: The method any of examples 55-66, wherein transmitting the electrical signal to the one or more tines using the conductor within the lumen comprises transmitting a separate electrical signal to each tine comprising a plurality of tines.

Example 68: The method any of examples 55-67, wherein extending one or more tines from the lead body comprises: extending a plurality of tines from the lead body, wherein each tine comprises a fixed end mechanically coupled to the drive shaft and each tine comprises a free end; and establishing a position of each free end different from a position of every other free end when the plurality of tines extends from the lead body.

Various examples of the disclosure have been described. Any combination of the described systems, operations, or functions is contemplated. These and other examples are within the scope of the following claims.

What is claimed is:

1. An implantable medical lead comprising;
a lead body comprising an interior surface defining a lumen, wherein the lead body defines a longitudinal axis;
a drive shaft configured to threadably engage the interior surface;
a torque member attached to the drive shaft and configured to rotate the drive shaft around the longitudinal axis, wherein the drive shaft is configured to translate in a direction substantially parallel to the longitudinal axis when the torque member rotates the drive shaft; and
one or more tines, wherein the one or more tines are configured to at least partially extend out of the lead body when the torque member rotates the drive shaft in a first direction and at least partially retract into the lumen when the torque member rotates the drive shaft in a second direction, and
wherein the lumen is sized to allow passage of the torque member and at least a portion of the drive shaft therethrough.

2. The implantable medical lead of claim 1, wherein the drive shaft is configured to translate the one or more tines in the direction substantially parallel to the longitudinal axis when the drive shaft translates in the direction substantially parallel to the longitudinal axis.

3. The implantable medical lead of claim 1, wherein the one or more tines is a plurality of tines, wherein each tine comprises a fixed end attached to the implantable medical lead and comprises a free end, wherein each tine is configured to establish a position of the free end different from a position of every other free end when the plurality of tines at least partially extends out of the lead body.

4. The implantable medical lead of claim 1, wherein the torque member comprises a torque coil.

5. The implantable medical lead of claim 1, wherein the torque member is configured to rotate relative to the interior surface when the torque member rotates the drive shaft.

6. The implantable medical lead of claim 1, wherein the drive shaft is configured to translate in the direction substantially parallel to the longitudinal axis relative to the interior surface.

7. The implantable medical lead of claim 1, wherein the lumen defined by the interior surface surrounds the longitudinal axis defined by the lead body.

8. The implantable medical lead of claim 1, further comprising a conductor coupled to the one or more tines and configured to extend through the lumen.

9. The implantable medical lead of claim 8, wherein:
the one or more tines is a plurality of tines,
the conductor is a multi-conductor comprising a plurality of conductors,
each tine in the plurality of tines is in electrical communication with at least one of the conductors in the plurality of conductors, and
each tine in the plurality of tines is electrically isolated from every other tine in the plurality of tines.

10. The implantable medical lead of claim 8, wherein the torque member defines a channel, and wherein the conductor passes through the channel.

11. The implantable medical lead of claim 10, wherein the torque member surrounds the channel and defines a distal opening of the channel at a distal end of the channel and a proximal opening of the channel at a proximal end of the channel, and wherein the torque member is sized to allow passage of the conductor through the distal end and the proximal end.

12. The implantable medical lead of claim 8, wherein the drive shaft defines a shaft channel, and wherein the conductor extends through at least some portion of the shaft channel.

13. The implantable medical lead of claim 1, wherein the drive shaft is configured to rotate relative to the interior surface and relative to the one or more tines when the torque member rotates the drive shaft.

14. The implantable medical lead of claim 1, wherein:
the drive shaft is configured to rotate relative to the interior surface when the torque member rotates the drive shaft, and
the one or more tines are rotationally coupled with the drive shaft.

15. The implantable medical lead of claim 1, wherein the drive shaft is between the one or more tines and the torque member.

16. An implantable medical lead comprising;
a lead body comprising an interior surface defining a lumen, wherein the lead body defines a longitudinal axis;
a drive shaft configured to threadably engage the interior surface;
a torque member configured to rotate the drive shaft around the longitudinal axis, wherein the torque member is configured to rotate relative to the interior surface, wherein the drive shaft is configured to translate in a direction substantially parallel to the longitudinal axis and relative to the interior surface when the torque member rotates the drive shaft, and wherein the torque member defines a channel; and one or more tines, wherein the one or more tines are configured to at least partially extend out of the lead body when the torque member rotates the drive shaft in a first direction and at least partially retract into the lumen when the torque member rotates the drive shaft in a second direction; and a conductor coupled to the one or more tines and configured to extend through the lumen, wherein the conductor passes through the channel of the torque member, wherein the lumen is sized to allow passage of the torque member and at least a portion of the drive shaft therethrough.

17. The implantable medical lead of claim 16, wherein the drive shaft is configured to rotate relative to the one or more tines when the torque member rotates the drive shaft.

18. The implantable medical lead of claim 16, wherein the one or more tines are rotationally coupled with the drive shaft.

19. A method of inserting one or more tines comprising:
rotating a torque member within a lumen of a lead body around a longitudinal axis defined by the lead body, wherein an interior surface of the lead body defines the lumen;

rotating a drive shaft rotationally coupled to the torque member using the rotation of the torque member, wherein the drive shaft is configured to threadably engage the interior surface, wherein the torque member is attached to the drive shaft, and wherein the drive shaft is configured to translate in a direction substantially parallel to the longitudinal axis when the torque member rotates the drive shaft;

threadably engaging the drive shaft and the interior surface;

converting the rotation of the drive shaft into a lateral translation of the drive shaft using the threaded engagement; and extending one or more tines from the lead body by translating the one or more tines using the lateral translation of the drive shaft, wherein the one or more tines are configured to at least partially extend out of the lead body when the torque member rotates the drive shaft in a first direction and at least partially retract into the lumen when the torque member rotates the drive shaft in a second direction, and wherein the lumen is sized to allow passage of the torque member and at least a portion of the drive shaft therethrough.

20. The method of claim 19, wherein converting the rotation of the drive shaft comprises rotating a set of external threads on the drive shaft using the rotation of the drive shaft.

* * * * *